US008805128B2

(12) United States Patent
Wild et al.

(10) Patent No.: US 8,805,128 B2
(45) Date of Patent: *Aug. 12, 2014

(54) MULTI-POINT PRESSURE SENSOR AND USES THEREOF

(71) Applicant: UVic Industry Partnership Inc., Victoria (CA)

(72) Inventors: Peter Martin Wild, Victoria (CA); Christopher Raymond Dennison, Victoria (CA); David Andrew Singlehurst, Victoria (CA); Chris Bueley, Victoria (CA)

(73) Assignee: UVic Industry Partnerships Inc., Victoria (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/632,305

(22) Filed: Oct. 1, 2012

(65) Prior Publication Data

US 2013/0022308 A1 Jan. 24, 2013

Related U.S. Application Data

(63) Continuation of application No. PCT/CA2011/000344, filed on Mar. 30, 2011.

(60) Provisional application No. 61/319,133, filed on Mar. 30, 2010.

(51) Int. Cl.
*G02B 6/00* (2006.01)

(52) U.S. Cl.
USPC .................. 385/12; 385/14; 385/15; 385/31; 385/37; 385/39

(58) Field of Classification Search
USPC ........................ 385/12, 13, 14, 15, 31, 37, 39
See application file for complete search history.

(56) References Cited

U.S. PATENT DOCUMENTS 4,988,212 A 1/1991 Sun et al.
5,124,130 A 6/1992 Costello et al.
(Continued)

FOREIGN PATENT DOCUMENTS

CA 2353452 A1 6/2000
CA 2353567 A1 6/2000
(Continued)

OTHER PUBLICATIONS

International Search Report and Written Opinion for PCT/CA2011/000344, dated Jun. 2, 2011, 9 pages.

(Continued)

*Primary Examiner* — Jennifer Doan
(74) *Attorney, Agent, or Firm* — Klarquist Sparkman, LLP (57) ABSTRACT

A sensing device for detecting a physical parameter exemplified by pressures, strains, temperatures, indices of refraction, and combinations thereof. The sensing device comprises a probe having a housing for sealably mounting therein an optical fiber. The optical fiber is provided at its distal end with at least two spaced apart fiber Bragg gratings. The proximal end of the probe is engagable with a holder, and is in communication with fiber Bragg grating interrogation systems. Spacers and seals may be provided about the optical fiber between the fiber Bragg gratings. An orifice may be provided and sealed with a resilient membrane to provide a contained airspace around each fiber Bragg grating. The contained airspace may be optionally filled with a fluid or a gas.

26 Claims, 9 Drawing Sheets

(56) References Cited

U.S. PATENT DOCUMENTS

| | | | |
|---|---|---|---|
| 6,282,338 B1 * | 8/2001 | Egalon | 385/28 |
| 6,337,737 B1 | 1/2002 | Chang et al. | |
| 6,396,572 B1 | 5/2002 | Chang et al. | |
| 6,563,970 B1 * | 5/2003 | Bohnert et al. | 385/13 |
| 6,580,511 B1 | 6/2003 | Discenzo | |
| 6,677,576 B1 | 1/2004 | Kenney et al. | |
| 6,854,327 B2 | 2/2005 | Rambow et al. | |
| 7,003,184 B2 | 2/2006 | Ronnekleiv et al. | |
| 7,196,318 B2 | 3/2007 | Shin et al. | |
| 8,205,504 B2 * | 6/2012 | Dennison et al. | 73/705 |
| 8,317,723 B2 * | 11/2012 | Dennison et al. | 600/561 |
| 2002/0041724 A1 | 4/2002 | Ronnekleiv et al. | |
| 2003/0227097 A1 | 12/2003 | Girardon et al. | |
| 2004/0129083 A1 | 7/2004 | Fernald et al. | |
| 2004/0182166 A1 | 9/2004 | Jones et al. | |
| 2004/0237648 A1 | 12/2004 | Jones et al. | |
| 2005/0263281 A1 | 12/2005 | Lovell et al. | |
| 2006/0011820 A1 | 1/2006 | Chow-Shing et al. | |
| 2006/0062510 A1 | 3/2006 | Arias Vidal et al. | |
| 2007/0147738 A1 | 6/2007 | Wang et al. | |
| 2009/0092351 A1 | 4/2009 | Goldner et al. | |
| 2010/0018703 A1 | 1/2010 | Lovell et al. | |
| 2011/0058768 A1 | 3/2011 | Swinehart et al. | |

FOREIGN PATENT DOCUMENTS

| | | |
|---|---|---|
| GB | 2371360 | 2/2005 |
| WO | WO 2007/095752 | 8/2007 |
| WO | WO 2009/140767 | 11/2009 |
| WO | WO 2011/120147 | 10/2011 |

OTHER PUBLICATIONS

Extended European Search Report for European Patent Application No. 09749371.2, dated Jun. 8, 2011, 4 pages.

International Search Report and Written Opinion for PCT/CA2007/000286, dated Jun. 6, 2007, 8 pages.

International Preliminary Report on Patentability for PCT/CA2007/000286, dated Aug. 26, 2008, 7 pages.

International Search Report and Written Opinion for PCT/CA2009/000701, dated Aug. 14, 2009, 7 pages.

International Preliminary Report on Patentability for PCT/CA2009/000701, dated Nov. 23, 2010, 6 pages.

International Preliminary Report on Patentability for PCT/CA2011/000344, dated Oct. 2, 2012, 8 pages.

* cited by examiner

MULTI-POINT PRESSURE SENSOR AND USES THEREOF

CROSS REFERENCE TO RELATED APPLICATIONS

This application is a continuation of PCT/CA2011/000344, filed Mar. 30, 2011, which was published in English under PCT Article 21(2), which in turn claims the benefit of U.S. Provisional Patent Application No. 61/319,133 filed on Mar. 30, 2010, both of which are incorporated herein by reference.

FIELD OF THE INVENTION

This present invention relates to devices for measuring fluid pressure in systems. More particularly, this invention relates to devices that incorporate multiple in-fibre Bragg gratings along a single optical fibre at various locations that are independently configured for measuring pressure at corresponding regions.

BACKGROUND OF THE INVENTION

A fibre Bragg grating is contained within the core of a short segment of optical fibre that reflects particular wavelength of light and transmits all others. The fundamental principle behind the operation of a fibre Bragg grating is Fresnel reflection. Light traveling between media of different refractive indices may both reflect and refract at the interface. This is achieved by successive perturbations to the effective refractive index in the core of the optical fibre. These perturbations to the effective refractive index lead to a reflection of a portion of the light which propagates along the fibre. Any changes in refractive index, as a result of strain within the fibre due to change in temperature, pressure and the like, will cause proportional shifts in the reflected spectra. A fibre Bragg grating can therefore be used as an inline optical filter to block certain wavelengths, or as a wavelength-specific reflector.

The Bragg wavelength is defined by Eq. 1

$$\lambda_B = 2 n_{eff} \Lambda \qquad \text{Eq. 1}$$

where $\Lambda$ is the grating period, $n_{eff}$ is the effective refractive index of the grating in the core of the fibre and $\lambda_B$ is the Bragg wavelength or the reflected wavelength. From this relationship, any changes to the grating period or the effective refractive index of the grating in the core of the fibre will cause a change in the Bragg wavelength.

In-fibre Bragg gratings are used extensively as sensors for various parameters including displacement, strain, pressure, humidity, radiation dose and temperature. Temperature-sensing using fibre Bragg grating works on the principles of thermal expansion and photo-thermal effect. Photo-thermal effect is the changing of the refractive index due to change in temperature, and thermal expansion is changing the grating period due to change in temperature. Pressure measurement is important in environmental applications, medical diagnostic, research and development, and many fields of engineering. Specifically, fibre Bragg gratings are useful in instrumentation applications such as seismology and down-hole sensors in oil and gas wells to measure the effects of external pressure, temperature, seismic vibrations and inline flow. As such, they offer a significant advantage over traditional electronic gauges used for these applications since they are less sensitive to vibration or heat, and consequently they are far more reliable.

Fibre Bragg gratings are an attractive alternative to other piezoelectric, resistive or other solid-state sensing technologies because they are small (typically 125 µm in diameter), mechanically compliant, intrinsically robust, chemically inert, resistant to corrosive environments, immune to electromagnetic interference, and are capable of simultaneous multi-parameter sensing when suitably configured. Moreover, fibre Bragg grating sensors can be multiplexed along a single optical fibre, thereby allowing spatially distributed measurements.

Fibre Bragg gratings are applied only on a limited basis in medical pressure measurement applications, primarily because bare fibre Bragg gratings possess low sensitivities to hydrostatic pressure and are only capable of resolving pressure variations of the order MPa. In an effort to increase the sensitivity of fibre Bragg gratings to pressure, mechanical amplification schemes such as polymer coatings around the fibre circumference, pressure spacers and diaphragms, and chemical etching that reduces the cross-sectional area of the optical fibre have been developed. Sensors utilizing these schemes have increased pressure sensitivity because the strain along the fibre Bragg gratings is concentrated relative to the case of a bare-fibre Bragg grating. Prior art has presented a glass-bubble (4 mm diameter) housed fibre Bragg grating sensor and a polymer coated fibre Bragg grating sensor all with major diameters of the millimeter order. Due to their increased size, these sensors are invasive for medical pressure measurement applications, and they do not retain the intrinsic benefits offered by fibre Bragg gratings.

The prior art discloses a medical sensor which has a biocompatible fibre optic sensor probe for invasive medical use that includes an optical fibre, a sensing location at which the fibre is configured to provide at least one detectable changeable optical property responsive to a strain within the fibre, and at least one sensing element which undergoes a volumetric change in response to an in-body parameter to be sensed. The sensing element is coupled to the fibre in such a way that the volumetric change induces strain within the fibre so as to vary the detectable changeable optical property. In one embodiment, a fibre Bragg grating is used and a thick polymer coating such as a compliant silicone is used as the sensing element. The polymer coating on the fibre increases the strain on the fibre when exposed to pressure on its outer cylindrical surface. The prior art also discloses a fibre Bragg grating-based intervertebral disc pressure sensor that has both amplified sensitivity to pressure (i.e. seven times that of a bare fibre) as well as a diameter of 400 µm and a sensing area of only 0.126 mm².

SUMMARY OF THE INVENTION

The exemplary embodiments of the present invention relate to pressure-sensing devices and temperature-sensing devices comprising optical fibres having fibre Bragg gratings.

An exemplary pressure-sensing device comprises an optical fibre sealed into a probe-type housing. The distal portion of the probe detects pressures. The proximal portion of the probe is mounted into a holder. The probe may be releasable mounted into the holder. A section of the optical fibre housed within the distal sensing portion of the probe has a plurality of spaced-apart fibre Bragg gratings.

According to an aspect, the sections of the optical fibre interposed the spaced-apart fibre Bragg gratings are provided with seals that engage the housing thereby providing a contained airspace about each fibre Bragg grating. The contained airspaces may be optionally filled with a fluid or a gas.

According to another aspect, an orifice may be provided in a portion of the housing about a section of the optical fibre having a fibre Bragg grating. The orifice may be sealed with a resilient material thereby providing a contained airspace about the fibre Bragg grating. The contained airspace may be optionally filled with a fluid or a gas.

According to another aspect, at least one of the spaced-apart fibre Bragg gratings is a pressure-sensing fibre Bragg grating.

According to another aspect, at least one of the spaced-apart fibre Bragg gratings is a temperature-sensing fibre Bragg grating.

According to another aspect, at least one of the spaced-apart fibre Bragg gratings is a pressure-sensing fibre Bragg grating, and at least one of the other spaced-apart fibre Bragg gratings is a temperature-sensing fibre Bragg grating.

The exemplary pressure-sensing devices of the present invention may be configured for sensing and measuring pressures in industrial applications exemplified by structural monitoring of buildings, roadworks, coverings and/or shells and/or structural components of equipment operating in high-stress environments. Some exemplary pressure-sensing devices of the present invention may be configured for non-invasive and/or minimally invasive biomedical applications exemplified by detection and measurement of pressure changes in and/or along and/or within cerebrospinal fluid, muscle compartments, blood-vessel arterial stents, and areas of intradiscal pressure, intracranial pressure, intramuscular pressure, intra-articular pressure, ventricular pressure, and the like thereof.

BRIEF DESCRIPTION OF THE DRAWINGS

The present invention will be described in conjunction with reference to the following drawings, in which.

DETAILED DESCRIPTION OF THE INVENTION

In describing the embodiments of the present invention, specific terminology is employed for the sake of clarity. The present version of the invention is not intended to be limited to the specific terminology selected. It is to be understood that each specific element includes all technical equivalents that operate in a similar manner to accomplish similar functions.

The exemplary embodiments of the present invention relate to etched fibre Bragg grating multi-point pressure sensors having multiple sensing locations along the length of a single optical fibre. The etching of the optical fibre leads to increased sensitivity to strain and facilitates the extremely small and uniform outer diameter of the sensing body. Some embodiments of the present invention are suitable for measuring pressure, strain, temperature, index of refraction and various other parameters using optical principles known in the prior art.

The exemplary etched multi-point fibre Bragg grating sensors of the present invention can be interfaced with typical fibre Bragg grating interrogation systems known to those skilled in the arts. Suitable applications include, but are not limited to: civil engineering, structural engineering, and environmental engineering applications, minimally invasive medical applications for detection and measurement of pressure changes in and/or along and/or within cerebrospinal fluid, muscle compartments, blood-vessel arterial stents, and areas of intradiscal pressure, intracranial pressure, intramuscular pressure, intra-articular pressure, ventricular pressure, and the like thereof.

The following are exemplary, but non-limiting examples which illustrate embodiments of the present invention.

Figure 1:
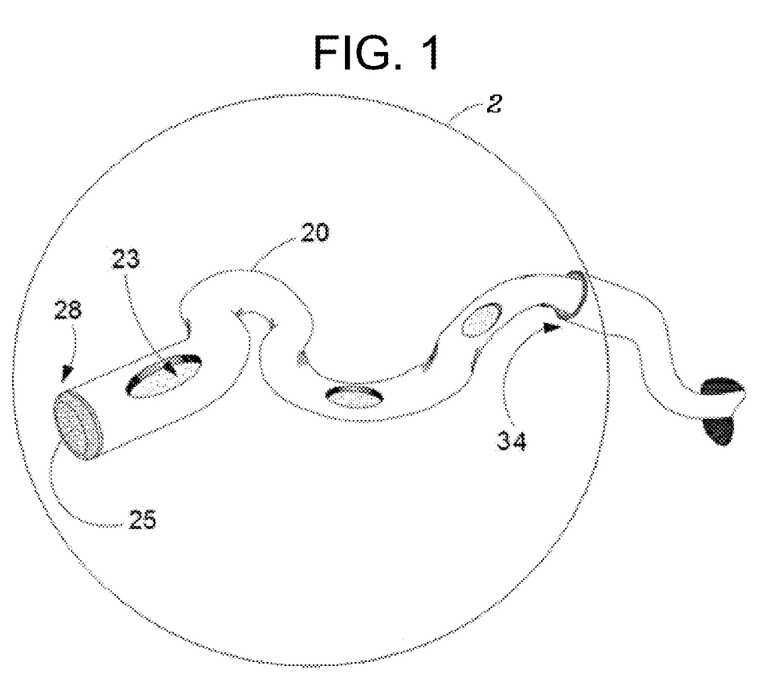
FIG. 1 is a perspective view of an exemplary etched multi-point fibre Bragg grating sensor of the present invention.

An exemplary embodiment of the present invention is shown in FIG. 1 wherein an etched multi-point sensor 2 has multiple sensing locations, each incorporating a fibre Bragg grating along the same length of etched optical fibre or etched portion thereof, along its length to simultaneously measure dynamic pressures at multiple positions along the length of the sensor body. The sensing region is located inside the orifice 23. The optical fibre was inserted into the housing 20. The housing 20 is preferably a stainless steel hypodermic tube. However, it is within the scope of the invention for other suitable materials known to those skilled in these arts to be configured as etched optical fibre housings. The proximal end 14 of the multi-point sensor 2 was interconnected to a fibre Bragg grating interrogation system (not shown). The multi-point sensor was terminated at the distal end 28. The distal end of the housing was sealed with a rigid plug comprised of epoxy 25. The plug 25 may be comprised of any suitable material that provides a rigid, incompressible and leak-tight seal around the distal end 28 of the housing 20. It is within the scope of the invention for other suitable materials known to those skilled in the art to configure a plug. When the multi-point sensor 2 is subjected to a pressure from a fluid medium, the force exerted on the sensing region surface causes tension within the optical fibre. This tension increases the strain in the etched section of optical fibre that contains the fibre Bragg grating resulting in a shift in the Bragg wavelength. It is worth noting there are other mechanisms, dilatation and strain-optic effect, responsible for inducing strain in the fibre thus affecting the reflected wavelength. Dilatation is the elongation of the optical fibre as a result of pressure exerted by the fluid medium on its surface, over the length that contains the Bragg grating. Strain-optic effect is the change in the refractive index profile along the length of optical fibre that contains the Bragg grating, caused by pressure induced strain. These two mechanisms are not discussed as their effects are constant, regardless of fibre diameter. They are inherent to FBG sensors not only of this design and their contribution to overall sensitivity is minimal compared with the pressure induced strain that is a direct result of the design features outlined in this invention.

Figure 2A:
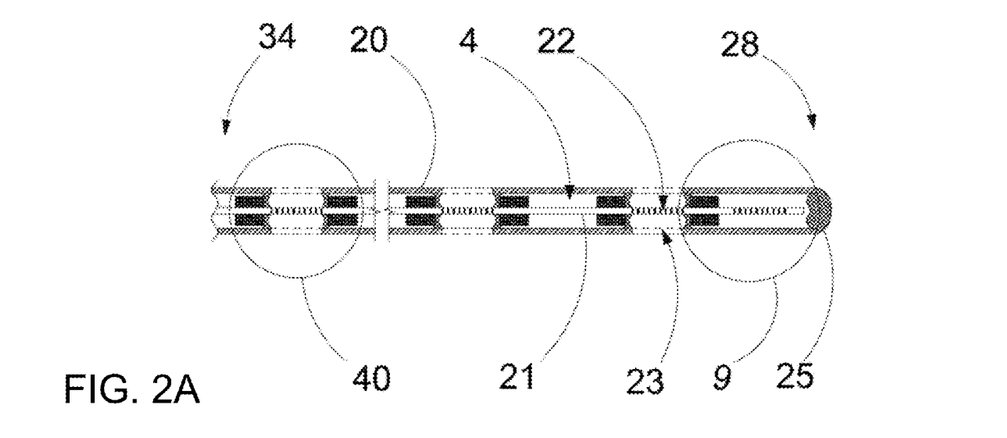
FIG. 2A is a cross-section view of exemplary etched multi-point fibre Bragg grating sensor of the present invention.
Figure 2B:
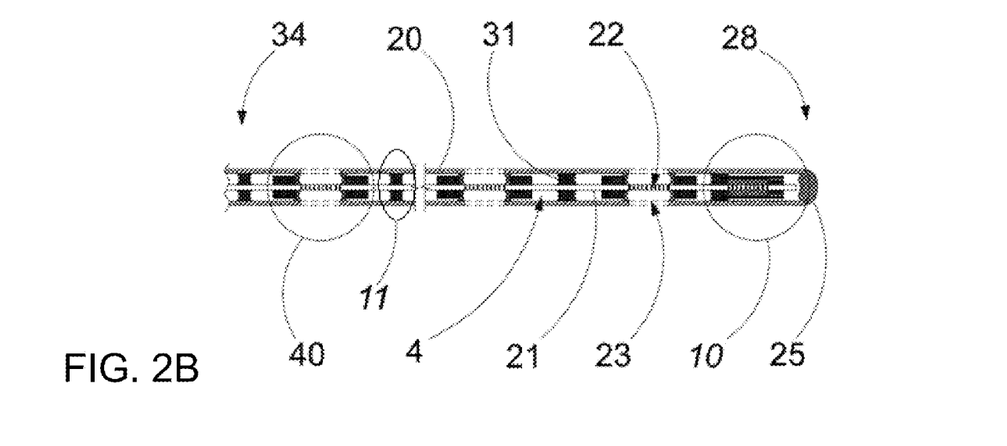
FIG. 2B is a cross-section view of another exemplary etched multi-point fibre Bragg grating sensor of the present invention.
Figure 11:
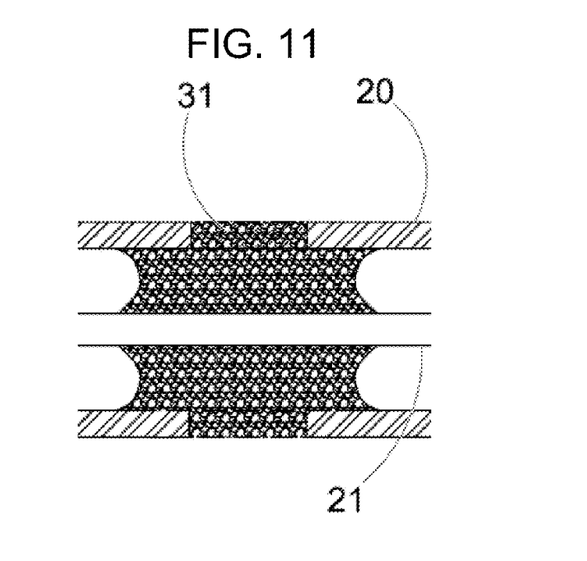
FIG. 11 is a close-up view of the anchor of the exemplary etched multi-point fibre Bragg grating sensor shown in FIG. 2B.

Another exemplary embodiment of the present invention is shown in FIG. 2A and FIG. 2B wherein an etched multi-point sensor comprises another design feature of the present invention. Multiple sensing regions, each containing a fibre Bragg grating 22 (Technica SA, Beijing, China) within a single length of etched optical fibre 21 (SMF-28 compatible, such as Corning Life Sciences, Lowell, Mass., USA) or etched portion thereof, can be incorporated along the length of the sensor body. At least one of these sensing locations may include a second fibre Bragg grating to compensate for temperature. Four sensing regions 40 are shown for simplicity; three sensing regions to measure dynamic pressure and one sensing region to measure temperature. Measuring the temperature of the fluid medium enables the interrogation system to compensate for any shift in the spectrum of the Bragg wavelength due to the changes in temperature. The optical fibre was inserted into the housing 20. The housing 20 is preferably a hypodermic tube. However, it is within the scope of the invention for other suitable materials known to those skilled in these arts to be configured as etched fibre Bragg grating housings. The optical fibre was inserted into the housing 20 until the tip of the optical fibre 21 was almost flush with the end of the housing 20. This end was identified as the distal end 28 of the multi-point sensor. The distal end of the housing was sealed with a rigid plug comprised of epoxy 25. The plug 25 may be comprised of any suitable material that provides a rigid, incompressible and leak-tight seal around the distal end 28 of the housing 20. It is within the scope of the invention for other suitable materials known to those skilled in the art to configure a plug. The annular volume 4 of the sensor body 20 is typically filled with air throughout its length except in the sensing region that lies directly beneath the orifices 23 of the sensor body 20. In this location, the fluid medium is free to enter the annular volume 4 through the orifices 23 in the sensor body 20 allowing pressure to act upon the fibre Bragg grating 22. However, it is within the scope of the present invention to saturate the annulus with a suitable selected gas or a suitable selected fluid. The proximal end of the multi-point sensor 34 was interconnected to a fibre Bragg grating interrogation system (not shown). A small orifice 23 was cut into the sensor housing 20 using a rotary tool. The shape and size of said orifice may vary according to the application and dimensions of the sensor. Those skilled in the art will understand there are other methods of creating a small orifice. The anchor 31 (FIG. 2B and FIG. 11) is another rigid material exemplified by epoxy and the like that attached the optical fibre to the hypodermic tube. The anchor 31 secures the optical fibre 21 to the hypodermic tube 20; hence, preventing micro bending or compression from one sensing region to affect the adjacent sensing region (cross talk). The anchor 31 is needed in applications where the sensing regions are in close proximity and bending or compression from one sensing region affects the adjacent sensing locations. The anchor 31 may be as physically close apart as possible from the sensing region. In applications that require the sensing regions to be far apart and bending or compression of one sensing region will not affect the adjacent sensing region, the anchor 31 can be omitted as shown in FIG. 2A. The anchor 31 and the rigid plug 25 may be composed of radio-opaque dye or may incorporate a location detector, which may be used to determine the accurate location and position of each sensing region. Radio-opaque markers, such as radio-opaque paint and the like, can be applied around the sensor body 20 in proximity to each sensing region 40. The radio opaque markers can be viewed on an x-ray. Those skilled in the art will understand there are other methods of accurately estimating the location or position of a sensing region. The sensor may contain numerous temperature and pressure sensing regions 40 along the length of the sensor. A sensor comprised of one or more or a combination of different design variation of sensing regions 40. The sensing regions 40 may be as close apart as physically possible or as far apart as physically possible.

Figure 3:
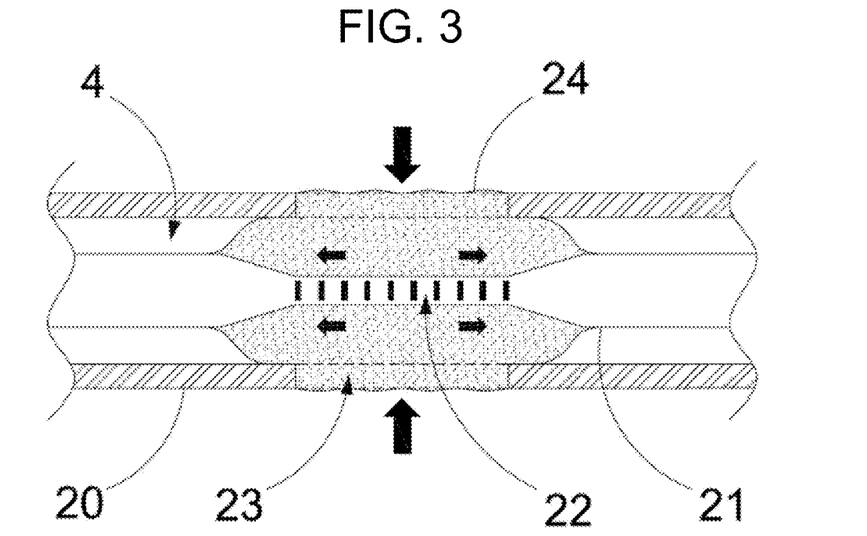
FIG. 3 is a cross-section view of a design variation of a sensing region of an exemplary etched multi-point fibre Bragg grating sensor.

Another exemplary embodiment of the present invention is shown in FIG. 3 illustrating a design variation to the sensing region 40 of the etched multi-point sensor of FIG. 2A and FIG. 2B. Multiple sensing regions, each containing a fibre Bragg grating 22 (Technica SA, Beijing, China) within a single length of etched optical fibre 21 (SMF-28 compatible, such as Corning Life Sciences, Lowell, Mass., USA) or etched portion thereof, may be incorporated along the length of the sensor body, whereby the exemplary embodiment illustrates a design variation of at least one of the sensing regions 40 shown in FIG. 2A and FIG. 2B. However, only one sensing region is shown for simplicity. The optical fibre was inserted into the housing 20. The housing 20 is preferably a stainless steel hypodermic tube. However, it is within the scope of the invention for other suitable materials known to those skilled in these arts to be configured as etched fibre Bragg grating housings. The annular volume 4 of the sensor body 20 is typically filled with air throughout its length except in the sensing region that lies directly beneath the orifices 23 of the sensor body 20. However, it is within the scope of the present invention to saturate the annulus with a suitable selected gas or a suitable selected fluid. A small orifice 23 was cut into the sensor housing 20 using a rotary tool. The shape and size of said orifice may vary according to the application and dimensions of the sensor. Those skilled in the art will understand there are other methods of creating a small orifice. The orifice 23 was then sealed with silicone sealant 24 to provide an air tight seal around the sensing region as well as a means to transmit pressure. Those skilled in the art will understand that a variety of natural and synthetic polymers are suitable for use as a resilient and compliant cover 24 for the orifice. The silicone sealant 24 may be composed of radio-opaque dye or may incorporate a location detector, which may be used to determine the accurate location and position of a sensing region. Radio-opaque markers, such as radio-opaque paint and the like, can be applied around the sensor body 20 in proximity to the sensing region. The radio opaque markers can be viewed on an x-ray. Those skilled in the art will understand there are other methods of accurately estimate the location of a sensing region. When the multi-point sensor was exposed to a hydrostatic pressure, the force acting upon the surface of the silicone sealant 24 by the pressurizing fluid was transmitted, via the sealant, through the orifice 23 and into the fibre 21. The increased strain within the optical fibre 21, likewise along the fibre Bragg grating 22, caused the reflected wavelength of the fibre Bragg grating 22 to change. This was measured with a suitable interrogation system and a purpose-made software program (LabView—National Instruments Corporation, Austin, Tex.). To increase sensitivity, the diameter of the optical fibre 21 was reduced through a chemical etching process known in the prior art.

Figure 4:
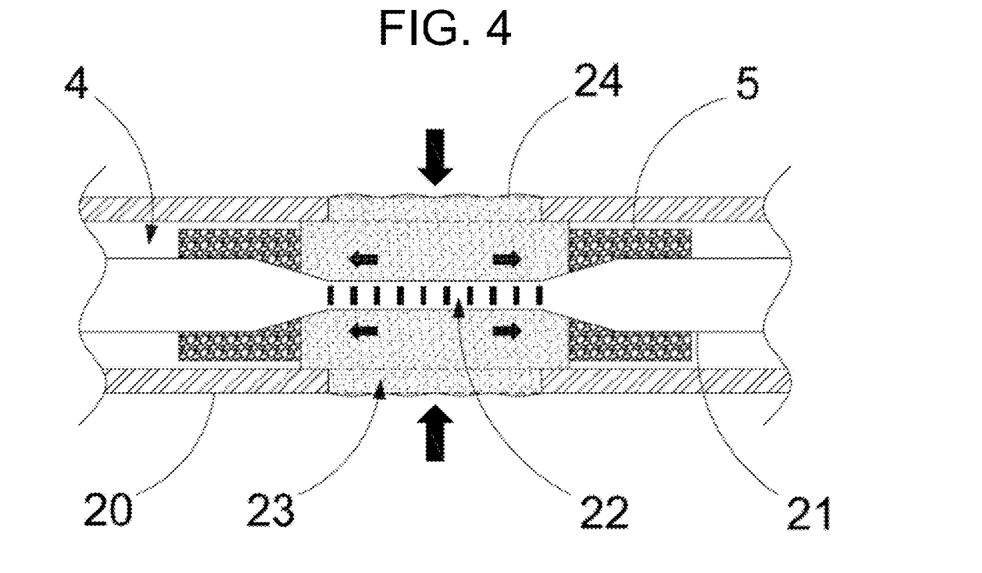
FIG. 4 is a cross-section view of another design variation of a sensing region of an exemplary etched multi-point fibre Bragg grating sensor.

Another exemplary embodiment of the present invention is shown in FIG. 4 illustrating a design variation to the sensing region 40 of the etched multi-point sensor of FIG. 2A and FIG. 2B. Multiple sensing regions, each containing a fibre Bragg grating 22 (Technica SA, Beijing, China) within a single length of etched optical fibre 21 (SMF-28 compatible, such as Corning Life Sciences, Lowell, Mass., USA) or etched portion thereof, may be incorporated along the length of the sensor body, whereby the exemplary embodiment illustrates a design variation of at least one of the sensing regions 40 shown in FIG. 2A and FIG. 2B. However, only one sensing region is shown for simplicity. The optical fibre was inserted into the housing 20. The housing 20 is preferably a stainless steel hypodermic tube. However, it is within the scope of the invention for other suitable materials known to those skilled in these arts to be configured as etched fibre Bragg grating housings. The annular volume 4 of the sensor body 20 is typically filled with air throughout its length except in the sensing region that lies directly beneath the orifices 23 of the sensor body 20. However, it is within the scope of the present invention to saturate the annulus with a suitable selected gas or a suitable selected fluid. A small orifice 23 was cut into the sensor housing 20 using a rotary tool. The shape and size of said orifice may vary according to the application and dimensions of the sensor. Those skilled in the art will understand there are other methods of creating a small orifice. Spacers 5 were affixed to the circumference of the etched optical fibre 21 on either side of the fibre Bragg grating 22. The spacers 5 increase the cross-sectional area upon which pressure from the silicone plug 23 may act upon, thus amplifying sensitivity of the fibre Bragg grating to pressure. The spacers 5 can be as large or as small as practicable and may be composed of a rigid material like epoxy. Those skilled in the art will understand that a variety of materials are suitable for use as spacers and likewise, several materials would be suitable as the bonding agent for said spacers. The spacers 5 are not attached to the hypodermic tubing 20. The orifice 23 was then sealed with silicone sealant 24 to provide an air tight seal around the sensing region as well as a means to transmit pressure. Those skilled in the art will understand that a variety of natural and synthetic polymers are suitable for use as a resilient and compliant cover 24 for the orifice. The silicone sealant 24 may be composed of radio-opaque dye or may incorporate a location detector, which may be used to determine the accurate location and position of a sensing region. Radio-opaque markers, such as radio-opaque paint and the like, can be applied around the sensor body 20 in proximity to the sensing region. The radio opaque markers can be viewed on an x-ray. Those skilled in the art will understand there are other methods of accurately estimate the location of a sensing region. When the multi-point sensor was exposed to a hydrostatic pressure, the force acting upon the surface of the silicone sealant 24 by the pressurizing fluid was transmitted, via the sealant, through the orifice 23 and into the fibre 21. The increased strain within the optical fibre 21, likewise along the fibre Bragg grating 22, caused the reflected wavelength of the fibre Bragg grating 22 to change. This was measured with a suitable interrogation system and a purpose-made software program (LabView—National Instruments Corporation, Austin, Tex.). To increase sensitivity, the diameter of the optical fibre 21 was reduced through a chemical etching process known in the prior art.

Figure 5:
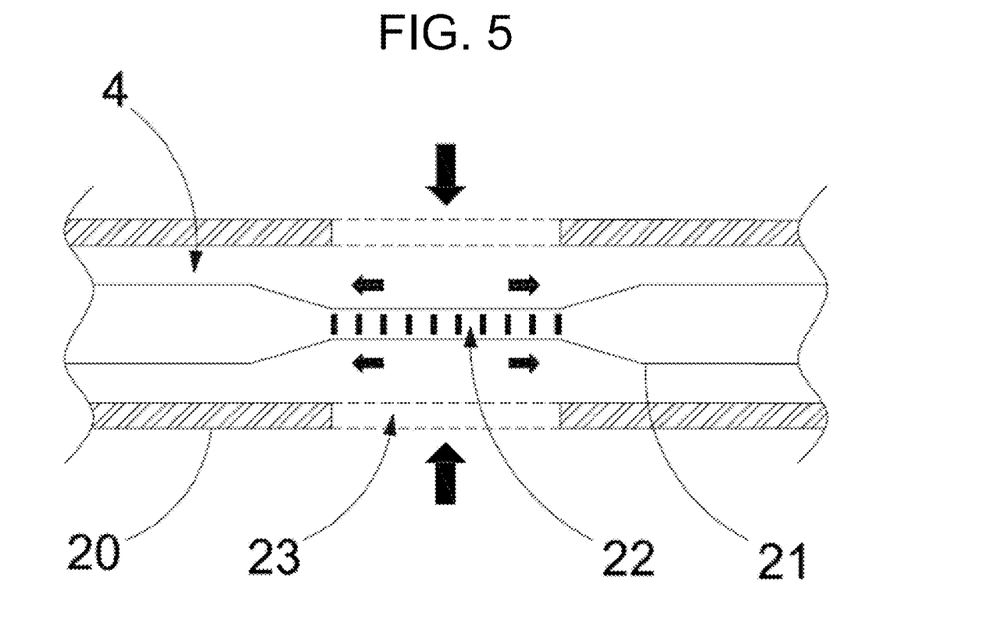
FIG. 5 is a cross-section view of another design variation of a sensing region of an exemplary etched multi-point fibre Bragg grating sensor.

Another exemplary embodiment of the present invention is shown in FIG. 5 illustrating a design variation to the sensing region 40 of the etched multi-point sensor of FIG. 2A and FIG. 2B. Multiple sensing regions, each containing a fibre Bragg grating 22 (Technica SA, Beijing, China) within a single length of etched optical fibre 21 (SMF-28 compatible, such as Corning Life Sciences, Lowell, Mass., USA) or etched portion thereof, may be incorporated along the length of the sensor body, whereby the exemplary embodiment illustrates a design variation of at least one of the sensing regions 40 shown in FIG. 2A and FIG. 2B. However, only one sensing region is shown for simplicity. The optical fibre was inserted into the housing 20. The housing 20 is preferably a stainless steel hypodermic tube. However, it is within the scope of the invention for other suitable materials known to those skilled in these arts to be configured as etched fibre Bragg grating housings. A small orifice 23 was cut into the sensor housing 20 using a rotary tool. The shape and size of the orifice may vary according to the application and dimensions of the sensor. Those skilled in the art will understand there are other methods of creating a small orifice. The fluid in which pressure is being measured is allowed to flow through the sensor body 20 via the orifices 23 and into the annular volume 4. The annular volume 4 is small enough to restrict fluid flow so that pressure is maintained within the fluid medium yet permitting relative motion between the sensor body 20 and optical fibre 21. The axial component of the pressure of the fluid medium acts upon the increasing cross-sectional area of the optical fibre, at the junction of etched and un-etched portions on either side of the fibre Bragg grating 22. As long as the pressure differential is maintained between the fluid surrounding the sensing region and the tip of the sensor, the fibre will be subjected to axial strain resulting in a change to the Bragg wavelength. Radio-opaque markers, such as radio-opaque paint and the like, can be applied around the sensor body 20 in proximity to the sensing region. The radio opaque markers can be viewed on an x-ray. Those skilled in the art will understand there are other methods of accurately estimate the location of a sensing region.

Figure 6:
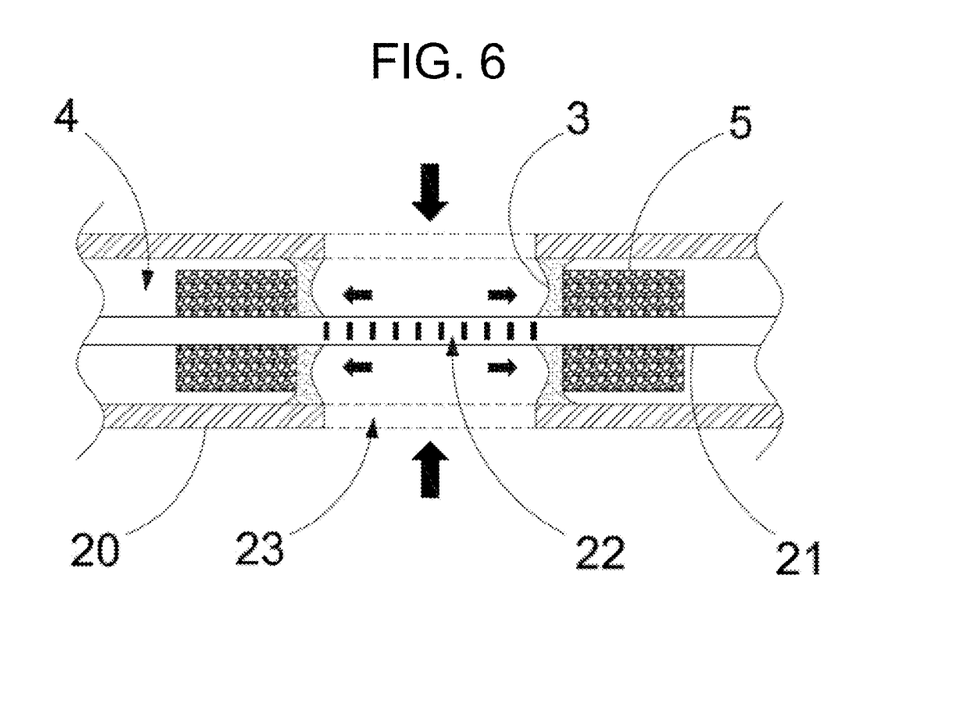
FIG. 6 is a cross-section view of another design variation of a sensing region of an exemplary etched multi-point fibre Bragg grating sensor.

Another exemplary embodiment of the present invention is shown in FIG. 6 illustrating a design variation to the sensing region 40 of the etched multi-point sensor of FIG. 2A and FIG. 2B. Multiple sensing regions, each containing a fibre Bragg grating 22 (Technica SA, Beijing, China) within a single length of etched optical fibre 21 (SMF-28 compatible, such as Corning Life Sciences, Lowell, Mass., USA) or etched portion thereof, may be incorporated along the length of the sensor body, whereby the exemplary embodiment illustrates a design variation of at least one of the sensing regions 40 shown in FIG. 2A and FIG. 2B. However, only one is shown for simplicity. The optical fibre was inserted into the housing 20. The housing 20 is preferably a hypodermic tube. However, it is within the scope of the invention for other suitable materials known to those skilled in these arts to be configured as etched fibre Bragg grating housings. The optical fibre was inserted into a housing 20 until the tip of the optical fibre 21 was almost flush with the end of the housing 20. A small orifice 23 was cut into the sensor housing 20 using a rotary tool. The shape and size of said orifice may vary according to the application and dimensions of the sensor. Those skilled in the art will understand there are other methods of creating a small orifice. Spacers 5 were affixed to the circumference of the etched optical fibre 21 on either side of the fibre Bragg grating 22. The spacers 5 can be as large or as small as practicable and may be composed of a rigid material like epoxy. Those skilled in the art will understand that a variety of materials are suitable for use as spacers and likewise, several materials would be suitable as the bonding agent for said spacers. The spacers 5 are not attached to the hypodermic tubing 20. The diaphragm 3 is comprised of a compliant material and is applied circumferentially to the optical fibre 21 and the spacers 5. The diaphragm 3 provides a flexible seal between the spacers 5 and the sensor housing 20 to contain the pressurizing fluid within the sensing region but also to allow for relative motion between the optical fibre 21 and sensor housing 20. The diameter of the optical fibre 21 is reduced by a chemical etching process known in the prior art. Although the annular volume 4 throughout the sensor body 20 is comprised mainly of air; in this configuration, fluid is permitted to fill the annulus around the sensing region. When the multi-point sensor is subjected to pressure from a fluid medium, the force exerted by the fluid on the inner surfaces of each spacer 5 causes tension within the optical fibre 21. This tension increases the strain in the fibre Bragg grating 22 resulting in a shift in the Bragg wavelength. Radio-opaque markers, such as radio-opaque paint and the like, can be applied around the sensor body 20 in proximity to the sensing region, which may be used to determine the accurate location and position of a sensing region. The radio opaque markers can be viewed on an x-ray. Those skilled in the art will understand there are other methods of accurately estimate the location of a sensing region.

Figure 7:
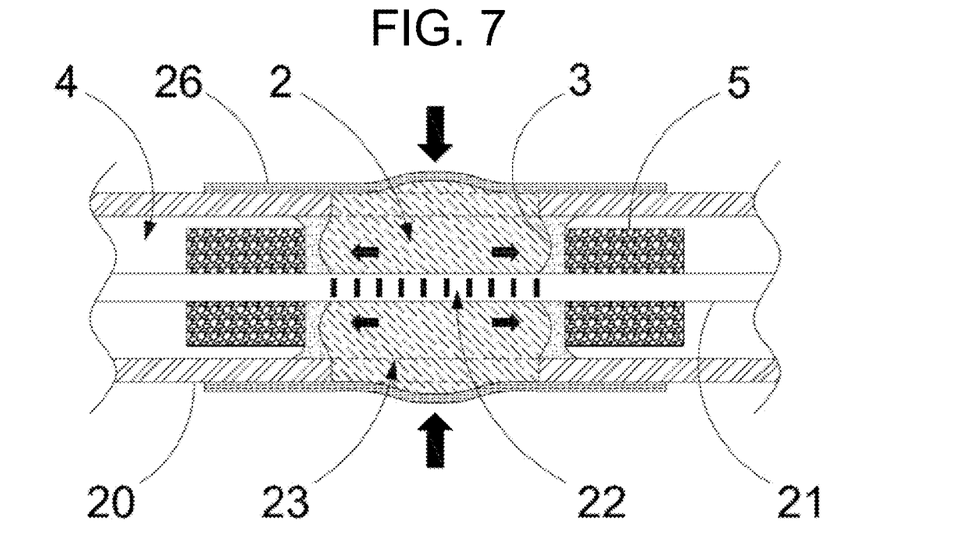
FIG. 7 is a cross-section view of another design variation of a sensing region of an exemplary etched multi-point fibre Bragg grating sensor.

Another exemplary embodiment of the present invention is shown in FIG. 7 illustrating a design variation to the sensing region 40 of the etched multi-point sensor of FIG. 2A and FIG. 2B. Multiple sensing regions, each containing a fibre Bragg grating 22 (Technica SA, Beijing, China) within a single length of etched optical fibre 21 (SMF-28 compatible, such as Corning Life Sciences, Lowell, Mass., USA) or etched portion thereof, may be incorporated along the length of the sensor body, whereby the exemplary embodiment illustrates a design variation of at least one of the sensing regions 40 shown in FIG. 2A and FIG. 2B. However, only one is shown for simplicity. The optical fibre was inserted into the housing 20. The housing 20 is preferably a hypodermic tube. However, it is within the scope of the invention for other suitable materials known to those skilled in these arts to be configured as etched fibre Bragg grating housings. The optical fibre was inserted into a housing 20 until the tip of the optical fibre 21 was almost flush with the end of the housing 20. A small orifice 23 was cut into the sensor housing 20 using a rotary tool. The shape and size of said orifice may vary according to the application and dimensions of the sensor. Those skilled in the art will understand there are other methods of creating a small orifice. The orifice 23 was then sealed with membrane heat shrink tubing 26 that allows for the sensing region to be leak tight. Those skilled in the art will understand that a variety of suitable materials can be used as a compliant cover for the orifice. Although the annular volume 4 between the proximal and distal ends of the sensor body 20 is comprised mainly of air, in this embodiment, the annulus around the etched portion of optical fibre 21 that contains the fibre Bragg grating 22 was filled with oil 2. Spacers 5 were affixed to the circumference of the etched optical fibre 21 on either side of the fibre Bragg grating 22. The spacers 5 can be as large or as small as practicable and may be composed of a rigid material like epoxy. Those skilled in the art will understand that a variety of materials are suitable for use as spacers and likewise, several materials would be suitable as the bonding agent for said spacers. The rigid material is not attached to the hypodermic tubing 20. The diaphragm 3 is comprised of a compliant material and is applied circumferentially to the optical fibre 21 and the spacers 5. The diaphragm 3 provides a flexible seal between the spacers 5 and the sensor housing 20 to contain the pressurizing oil 2 within the sensing region while allowing relative motion between the optical fibre 21 and sensor housing 20. When the multi-point sensor is subjected to pressure from a fluid medium, the force exerted by the fluid on the surface of the membrane 26 pressurizes the oil 2. The pressure from the oil 2 exerts an axial force on the inner surfaces of each spacer 5 causing a tension within the optical fibre 21. This tension increases the strain within the section of etched optical fibre 21 that contains the fibre Bragg grating 22 resulting in a change in the Bragg wavelength. Radio-opaque markers, such as radio-opaque paint and the like, can be applied around the sensor body 20 in proximity to the sensing region, which may be used to determine the accurate location and position of a sensing region. The radio opaque markers can be viewed on an x-ray. Those skilled in the art will understand there are other methods of accurately estimating the location of a sensing region.

Figure 8:
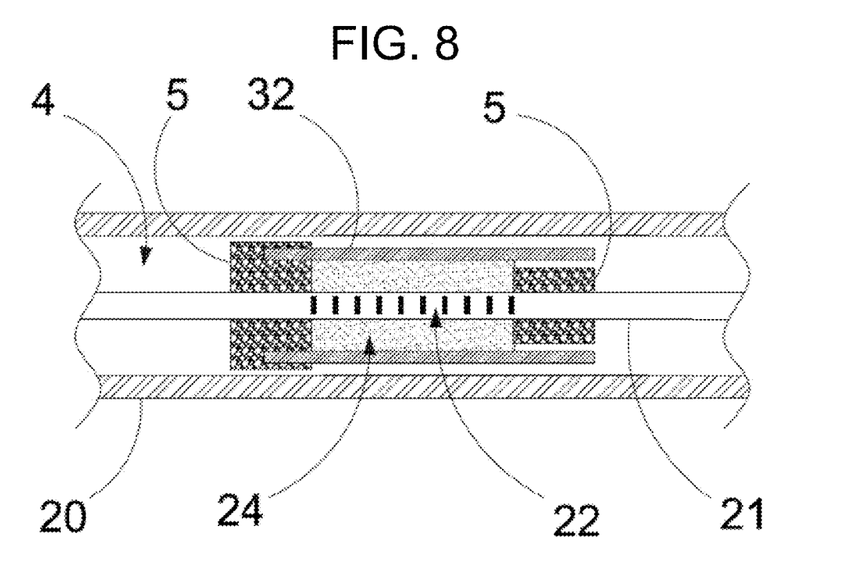
FIG. 8 is a cross-section view of another design variation of a sensing region of an exemplary etched multi-point fibre Bragg grating sensor.
Figure 9:
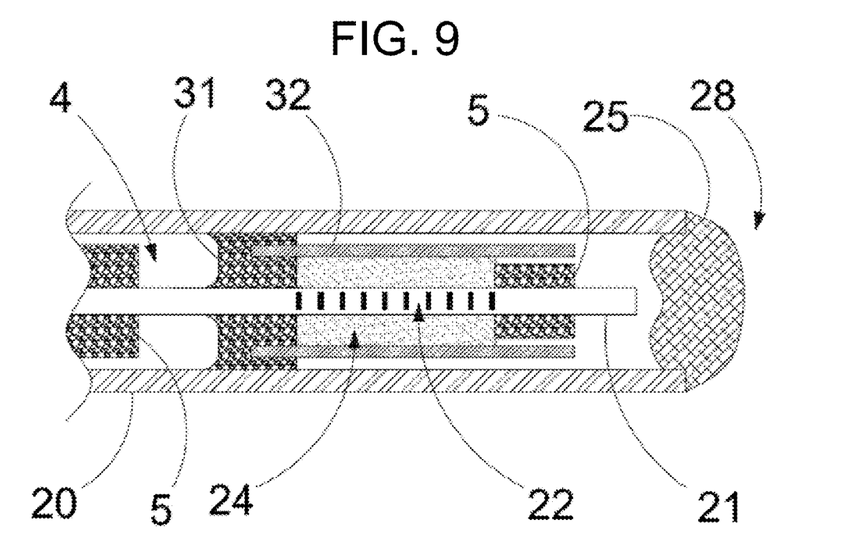
FIG. 9 is a close-up view of the temperature sensing region of the exemplary etched multi-point fibre Bragg grating sensor shown in FIG. 2B.
Figure 10:
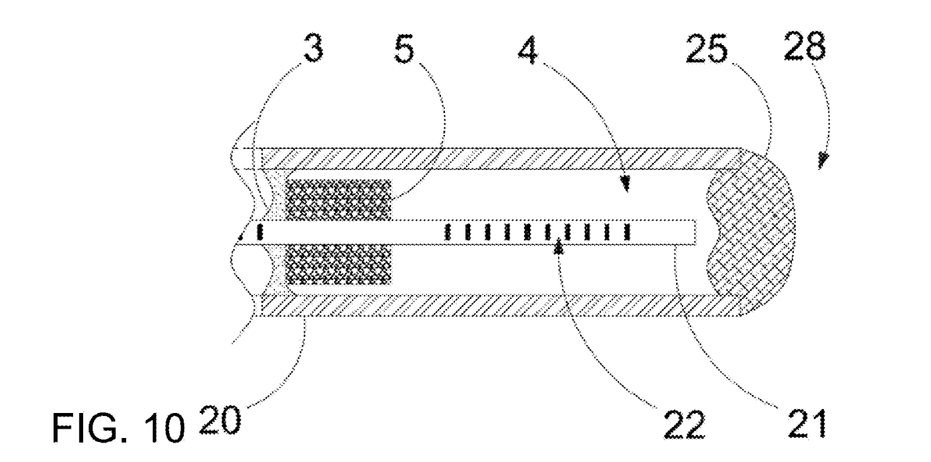
FIG. 10 is a close-up view of the temperature sensing region of the exemplary etched multi-point fibre Bragg grating sensor shown in FIG. 2A.

Another exemplary embodiment of the present invention is shown in FIG. 8 illustrating a design variation to the sensing region 40 of the etched multi-point sensor of FIG. 2A and FIG. 2B. Multiple sensing regions, each containing a fibre Bragg grating 22 (Technica SA, Beijing, China) within a single length of etched optical fibre 21 (SMF-28 compatible, such as Corning Life Sciences, Lowell, Mass., USA) or etched portion thereof, may be incorporated along the length of the sensor body, whereby the exemplary embodiment illustrates a design variation of at least one of the sensing regions 40 shown in FIG. 2A and FIG. 2B. The sensing region monitors the temperature change in the fluid medium. Measuring the temperature of the fluid medium enables the interrogation system to compensate for any shift in the spectrum of the Bragg wavelength due to the changes in temperature. The optical fibre was inserted into the housing 20. The housing 20 is preferably a hypodermic tube. However, it is within the scope of the invention for other suitable materials known to those skilled in these arts to be configured as etched fibre Bragg grating housings. The annular volume 4 is filled with air. However, it is within the scope of the present invention to saturate the annulus with a suitable selected gas or a suitable selected fluid. A compliant plug 24 exemplified by silicone and the like with a relatively high coefficient of thermal expansion was contained around the optical fibre 21 by a glass capillary tube 32 and by two rigid spacers 5 positioned on either side of the temperature compensating fibre Bragg grating 22. The capillary glass tube 32, which has a relatively low coefficient of thermal expansion, concentrates the thermal expansion of the compliant plug to the axial direction along the length of the portion of optical fibre 21 which contains the temperature compensating fibre Bragg grating 22. The glass capillary tube 32 also reduces the effect that bending of the sensor body has on the optical fibre 21. It is within the scope of the invention to those skilled in the art to use other suitable materials as a tube, and other suitable materials with a relatively high coefficient of thermal expansion such as silicone. A spacer 5 was anchored to the optical fibre 21 but not to the glass tube 32 permitting any volumetric change of the compliant plug 24 to exert strain along the length of optical fibre 21. The other spacer 5 can act as an anchor 31 by securing the capillary glass tube 32, the optical fibre 21 and the hypodermic tube 20 together as shown in FIG. 9 or it may only secure the capillary glass tube 32 to the optical fibre 21 as shown in FIG. 8 by a rigid plug comprised of epoxy. This single point of contact between the optical fibre 21 and sensor housing 20 limits the amount of strain induced into the optical fibre 21 by the thermal expansion of the stainless steel tube 20. It also shields the temperature compensating fibre Bragg grating 22 from the effects of pressure of the fluid medium. The spacers 5 can be as large or as small as practicable and may be composed of a rigid material like epoxy. Those skilled in the art will understand that a variety of materials are suitable for use as spacers and likewise, several materials would be suitable as the bonding agent for said spacers. The anchor 31 (FIG. 9) may be composed of radio-opaque dye or may incorporate a location detector, which may be used to determine the accurate location and position of a sensing region. Radio-opaque markers, such as radio-opaque paint and the like, can be applied around the sensor body 20 in proximity to the sensing region. The radio opaque markers can be viewed on an x-ray. Those skilled in the art will understand there are other methods of accurately estimate the location of a sensing region. When the multi-point sensor is subjected to a fluid medium, the temperature of the fluid will cause the silicone 24 to expand or contract, resulting in an axial force being exerted on the inner surfaces of each spacer 5. The direction of this force will cause either increasing or decreasing strain within the optical fibre 21 and thus within the temperature compensating fibre Bragg grating 22, resulting in a shift of the Bragg wavelength.

Figure 12:
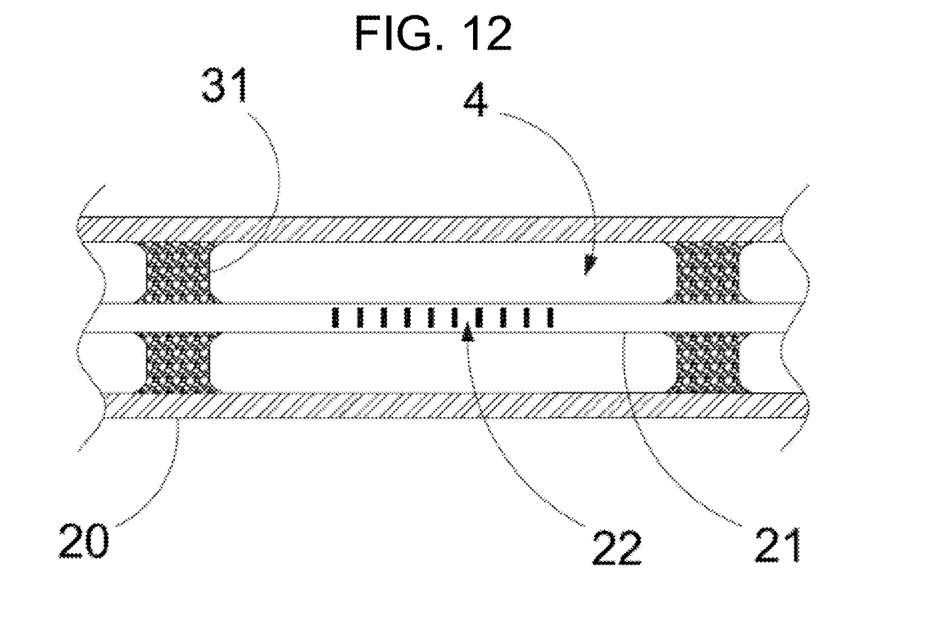
FIG. 12 is a cross-section view of another design variation of a sensing region of an exemplary etched multi-point fibre Bragg grating sensor.
Figure 13:
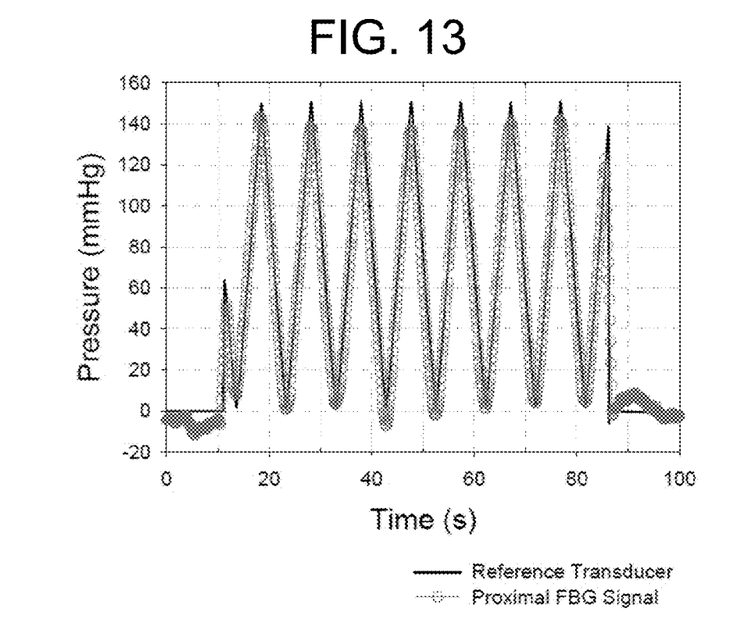
FIG. 13 is a graph illustrating the proximal fibre Bragg grating cyclic pressure response of an exemplary embodiment of the present invention.
Figure 14:
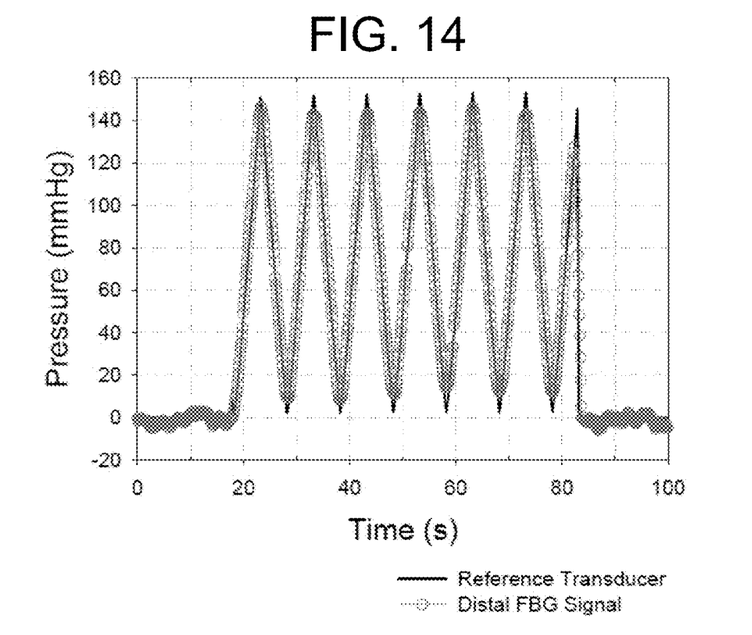
FIG. 14 is a graph illustrating the distal fibre Bragg grating cyclic pressure response of an exemplary embodiment of the present invention.

Another exemplary embodiment of the present invention is shown in FIG. 12 illustrating a design variation to the sensing region 40 of the etched multi-point sensor of FIG. 2A and FIG. 2B. Multiple sensing regions, each containing a fibre Bragg grating 22 (Technica SA, Beijing, China) within a single length of etched optical fibre 21 (SMF-28 compatible, such as Corning Life Sciences, Lowell, Mass., USA) or etched portion thereof, may be incorporated along the length of the sensor body, whereby the exemplary embodiment illustrates a design variation of at least one of the sensing regions 40 shown in FIG. 2A and FIG. 2B. The sensing region monitors the temperature change in the fluid medium. Measuring the temperature of the fluid medium enables the interrogation system to compensate for any shift in the spectrum of the Bragg wavelength due to the changes in temperature. The optical fibre was inserted into the housing 20. The housing 20 is preferably a hypodermic tube. However, it is within the scope of the invention for other suitable materials known to those skilled in these arts to be configured as etched fibre Bragg grating housings. The optical fibre was inserted into the housing 20 until the tip of the optical fibre 21 was almost flush with the end of the housing 20. The annular volume 4 between the proximal and distal end was filled with air. However, it is within the scope of the present invention to saturate the annulus with a suitable selected gas or a suitable selected fluid. The anchor 31 is another rigid material exemplified by epoxy and the like that attached the optical fibre to the hypodermic tube. The anchor 31 secures the optical fibre 21 to the hypodermic tube 20. The anchor 31 may be as physically close apart as possible from the sensing region 40. The anchor 31 may be composed of radio-opaque dye or may incorporate a location detector, which may be used to determine the accurate location and position of a sensing region. The radio opaque markers can be viewed on an x-ray. Those skilled in the art will understand there are other methods of accurately estimate the location of a sensing region. Those skilled in the art will understand that a variety of materials are suitable for use as anchors. The diameter of the optical fibre 21 is reduced by a chemical etching process known in the prior art. The temperature compensating fibre Bragg grating 22 is isolated from the fluid medium and it is unaffected by fluid pressure. A change in temperature of the fluid medium will cause the temperature compensating fibre Bragg grating 22 to contract or expand resulting in an axial force being exerted on the Bragg grating. This force will either increase strain or decrease strain within the fibre Bragg grating 22 and result in a shift of its Bragg wavelength. This temperature related shift in the Bragg wavelength of the temperature compensating fibre Bragg grating 22 may be used to compensate for the temperature related shift in the Bragg wavelength of the pressure-sensing region of the sensor. By determining the shift in wavelength due to temperature, the actual pressure of the fluid medium can be determined. Radio-opaque markers, such as radio-opaque paint and the like, can be applied around the sensor body 20 in proximity to the sensing region, which may be used to determine the accurate location and position of a sensing region. The radio opaque markers can be viewed on an x-ray. Those skilled in the art will understand there are other methods of accurately estimate the location of a sensing region.

What is claimed is:

1. A sensing device for detecting a physical parameter, the sensing device comprising:
    a probe comprising a housing for sealably mounting a sensor therethrough, the probe having a distal portion configured for detecting a physical parameter and a proximal portion configured to be coupled to a signal processing device;
    a sensor comprising an optical fibre extending therealong, the optical fibre having a section extending along a distal portion wherein the fibre is provided with one or more spaced-apart fibre Bragg gratings;
    a resilient membrane situated adjacent an end of the associated fibre Brace crating and sealed to the housing;
    a spacer affixed to the fibre and secured to the resilient membrane so as to be translatable along a length of the housing; and
    a holder configured for engaging a proximal portion of the probe whereby a distal portion of the probe extends from the holder.

2. The sensing device according to claim 1, further comprising;
    at least one orifice provided in the housing and situated at an associated fibre Bragg grating,
    wherein the physical parameter is one of a pressure, a strain, a temperature, an index of refraction, and combinations thereof.

3. The sensing device according to claim 2, wherein the spacer is affixed to a distal surface of the resilient membrane with respect to the fibre Bragg grating.

4. The sensing device according to claim 2, wherein the spacer is affixed to a proximal surface of the resilient membrane with respect to the fibre Bragg grating.

5. The sensing device according to claim 2, wherein the resilient membrane is annular and includes a portion situated between an outer surface of the spacer and an inner surface of the housing.

6. The sensing device according to claim 5, wherein the spacer is a cylindrical section that is sealed to the optical fibre.

7. The sensing device according to claim 5, wherein the resilient membrane is sealed to the optical fibre.

8. The sensing device according to claim 2, wherein the resilient membrane surrounds the fibre Bragg grating and fills the orifice.

9. The sensing device according to claim 1, further comprising:
    at least one orifice provided in the housing and situated at an associated fibre Bragg grating;

first and second resilient membranes situated adjacent first and second ends of the associated fibre Bragg grating, respectively, the first and second resilient membranes sealed to the housing; and first and second spacers affixed to the fibre, the first and second spacers secured to the first and second resilient membranes, respectively, so as to be translatable along a length of the housing, wherein the physical parameter is one of a pressure, a strain, a temperature, an index of refraction, and combinations thereof.

10. The sensing device according to claim 1, wherein an anchor comprising a rigid material is engaged with the optical fibre therebetween each of two or more spaced-apart fibre Bragg gratings.

11. The sensing device according to claim 1, wherein a seal is interposed between each of two or more spaced-apart fibre Bragg gratings, said seal engaging the housing and the optical fibre.

12. The sensing device according to claim 11, wherein an orifice is provided in the housing about each spaced-apart fibre Bragg grating.

13. The sensing device according to claim 12, wherein said orifice is filled and sealed with a resilient material.

14. The sensing device according to claim 12, wherein said orifice is sealingly engaged with a resilient membrane thereby providing a contained annulus thereabout said fibre Bragg grating.

15. The sensing device according to claim 14, wherein said contained annulus is filled with either a fluid or a gas or both a fluid and a gas.

16. The sensing device according to claim 1 further comprising a second fibre Bragg grating for measuring temperature.

17. The sensing device according to claim 1, wherein the optical fibre has a plurality of sections extending along the distal portion wherein each section is provided with a narrowed fibre diameter, and each narrowed-diameter section is provided with a fibre Bragg grating.

18. The sensing device according to claim 17, wherein a seal is interposed between each of said two or more spaced-apart fibre Bragg gratings, said seal engaging the housing and the optical fibre.

19. The sensing device according to claim 17, wherein a seal is interposed between each of said two or more spaced-apart fibre Bragg gratings, said seal engaging the housing and the optical fibre, said seal providing an airspace interposed between each fibre Bragg grating and the housing.

20. The sensing device according to claim 1, wherein the sensing device comprises a radio-opaque dye in proximity of the sensing region.

21. A sensing device, comprising:
a housing having a distal portion and a proximal portion configured to be coupled to a signal processing device;
a sensor comprising an optical fibre having a section that includes at least one sensing region, wherein the optical fibre is situated within the housing and the housing includes an orifice situated at the at least one sensing region;
a pair of rigid spacers affixed to the fibre, wherein the spacers are situated at a distal end and a proximal end of the at least one sensing region; and
a resilient membrane that surrounds the at least one sensing region and extends from the optical fiber so as to fill the orifice.

22. The sensing device of claim 21, wherein the resilient membrane is secured to an interior surface of the housing at the distal end and the proximal end of the at least one sensing region.

23. The sensing device of claim 22, wherein the resilient membranes are sealed to corresponding rigid spacers.

24. The sensing device of claim 22, wherein the resilient membranes are sealed to the optical fibre at the distal end and the proximal end of the at least one sensing region.

25. The sensing device of claim 21, further comprising a pair of anchors situated so as to secure the optical fibre to the interior surface of the housing at opposite ends of the at least one sensing region.

26. The sensing device of claim 21, wherein the at least one sensing region includes a fibre Bragg grating.

* * * * *